United States Patent
Leber et al.

(10) Patent No.: US 6,255,116 B1
(45) Date of Patent: Jul. 3, 2001

(54) APPARATUS AND PROCESS FOR ARRAYING BEADS

(75) Inventors: Jack Dale Leber, Doylestown, PA (US); Brian E. Lock, Princeton, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/212,538

(22) Filed: Dec. 17, 1998

(51) Int. Cl.[7] ................................................. G01N 35/10
(52) U.S. Cl. .......................... 436/54; 422/63; 422/65; 422/100; 436/43; 436/47; 436/49; 436/180
(58) Field of Search ........................... 422/63–65, 100, 422/43, 47, 54, 69, 174, 180, 49

(56) References Cited

U.S. PATENT DOCUMENTS

| | | | |
|---|---|---|---|
| 4,937,048 | * | 6/1990 | Sakai et al. ........................ 422/63 |
| 5,183,638 | * | 2/1993 | Wakatake ........................... 422/64 |
| 5,399,745 | * | 3/1995 | Yoneoka et al. ................... 560/239 |
| 5,722,470 | * | 3/1998 | Kedar ................................. 141/100 |
| 5,813,760 | * | 9/1998 | Strong ............................... 366/258 |
| 5,935,859 | * | 8/1999 | Elliott et al. ........................ 436/54 |

FOREIGN PATENT DOCUMENTS

97/40383 * 10/1997 (WO) .

* cited by examiner

Primary Examiner—Arlen Soderquist
(74) Attorney, Agent, or Firm—S. Venetainer

(57) ABSTRACT

A mixture of beads from a combinatorial library is held in suspension in a liquid by movement of the liquid induced by a vertically reciprocating paddle. The tips of needles in an array are immersed in the suspension, a slot being provided in the paddle to avoid collision with the needles. Liquid is drawn into the needles until a bead becomes attached to the tip of each needle. Excess beads adhering to the needles are shaken off by an electromagnetically operated vibrator, and the beads are deposited in wells of a well plate by applying a short burst of pressure to the interiors of the needles. Liquid and any debris within the needles are thereafter discharged to a receptacle by applying a higher pressure burst to the interiors of the needles.

8 Claims, 5 Drawing Sheets

APPARATUS AND PROCESS FOR ARRAYING BEADS

FIELD OF THE INVENTION

This invention relates generally to the handling of beads and more particularly to an improved process and apparatus for depositing such beads in two-dimensional arrays.

BACKGROUND OF THE INVENTION

Synthesis of combinatorial compound libraries on bead supports is a well-established method for generating chemical diversity for screening against targets of pharmacological relevance. Such libraries may be synthesized as bulk populations or discrete sublibraries with or without identifier tags for deconvolution. In most cases each bead carries a single unique compound and is present in a mixture of beads containing other compounds. To test the beads for activity against a pharmacological target, it is desirable to separate the beads so that each bead may be individually assayed against one or more targets. The beads carrying active compounds can be identified and the structures of the compounds elucidated. It is also desirable to separate the beads into arrays that are geometrically compatible with robotic screening systems, for example 8×12 arrays or other formats such as 384 or 896-well configurations.

Current methods of bead arraying include manual picking and hydrodynamic sorting in which beads are allowed to flow though an aperture and once detected are deposited into assay wells. Manual picking is slow and tedious. Hydrodynamic methods heretofore in use have been slow and the equipment is prone to clogging. Buoyancy variations within the bead library are also known to cause problems in hydrodynamic sorting. A problem common to the prior methods is that, because the beads are extremely small, typically 300 $\mu$m(0.3 mm) or smaller, there is a tendency for two or more beads, carrying different compounds, to be deposited occasionally at a single location in the array. Still another problem encountered in bead arraying is that the beads tend to be fragile, and can be broken up into fragments especially when mechanically agitated.

These problems have recently been addressed in a bead picking apparatus by which beads are picked individually from a suspension of beads in a liquid. The suspension can be established by releasing gas bubbles from orifices at the bottom of a vessel to keep the liquid in motion. Alternatively, two immiscible liquids can be used, one having a density greater than that of the beads and the other having a density lower than that of the beads. The beads are suspended at the interface of the two liquids.

The bead picking apparatus comprises a set of hollow needles. Liquid is drawn from the suspension into the internal passages of the needles through openings at an ends of the internal passages, each opening being of a size smaller than any one of the beads and shaped so that it can be substantially closed off by a bead. When a bead closes off the opening, a pressure differential is established such that the external pressure exerted on the bead closing off the opening is greater than the pressure within the passage, and the bead is thereby held in engagement with the opening. The set of needles is then withdrawn from the vessel with the beads in engagement with the openings, and the beads can then be released and deposited into wells at a remote location.

The procedure just described has been used successfully, but has certain drawbacks. It is difficult to use gas bubbles to prevent settling of beads. Elaborate measures must be taken in order for gas bubbles to keep beads in suspension. For example, the vessel for containing the suspension of beads may be constructed with separate compartments, one for each needle in the picking apparatus. The compartments have sloping walls, and each compartment has its own gas-releasing orifice. This arrangement does not lend itself readily to use with a bead picker in which the needles are very close to one another. Therefore, in the case in which beads were to be deposited in a conventional well plate having eight columns of wells, it was necessary to use a picker comprising four needles spaced from one another so that they were alignable with every other well in a row of eight wells, and to index the picker laterally in order to deposit beads in odd-numbered wells of a row in a first step, and thereafter deposit beads in the even-numbered wells of the same row.

In the case of immiscible liquids it is difficult to achieve a satisfactory spatial distribution of beads at the liquid-liquid interface so that beads readily become attached to every needle of the bead picker.

Another difficulty encountered with the prior bead picking apparatus is that excess beads adhering to the needles are jarred loose by stopping the picker suddenly, or by bringing the needles into contact with a stop. Using this method, the excess beads not readily dislodged without a significant risk of dislodging the desired beads attached to the openings of the needles.

Still another difficulty with the prior bead picking apparatus is the clogging that can occur especially in the case in which a needle picks up a broken bead.

SUMMARY OF THE INVENTION

The principal object of this invention is to provide a bead arraying apparatus having improved reliability. Further objects of the invention include avoiding the deposition of unwanted beads into wells, the avoidance of empty wells, and the avoidance of clogging of the picker needles, especially by broken beads.

The bead arraying apparatus in accordance with the invention comprises a bead supply vessel containing a mixture comprising beads in a liquid, and a paddle within the vessel and immersed in the liquid therein. An air cylinder, motor, or other suitable device effects reciprocation of the paddle within the liquid so that the beads are maintained in suspension in the liquid by movement of the liquid induced by the paddle as it reciprocates.

Preferably, the horizontal projection of the paddle has an area sufficient in comparison to the horizontal cross-sections of the vessel that movement of the paddle within the liquid in a substantially vertical path induces a substantial vertical movement of the liquid. The means for effecting reciprocating movement of the paddle preferably moves the paddle in a substantially vertical path, whereby the beads are maintained in suspension in the liquid by the substantial vertical movement of the liquid induced by the paddle as it reciprocates.

The apparatus also includes an array of suitable hollow elements, preferably elongated needles spaced from one another. Each hollow element has an internal passage and an opening at an end of the internal passage. Each of the openings is circular in shape so that it can be substantially closed off by a spherical bead. The array is insertable into the vessel so that all of the openings of the elements are immersed in the liquid within the vessel. A pump or other suitable means is provided for drawing liquid from the vessel into the internal passages of the hollow elements through their openings to establish a pressure differential across each opening such that the external pressure exerted on a bead closing off the opening of each hollow element is greater than the pressure within the passage of the same hollow element. The pressure difference holds the bead in engagement with the opening at least while the opening is immersed in liquid. A robot arm or other suitable means is provided for withdrawing the array of hollow elements from the vessel with beads in engagement with the openings thereof and for moving the array to a remote location for deposition of the beads.

In the case of elongated needles spaced from one another, the needles preferably extend parallel to one another, and the paddle preferably comprises at least one opening through which the needles can extend when the needles are inserted into the vessel. The opening allows the reciprocating movement of the paddle to continue as the needles are immersed in the vessel. The reciprocating movement of the paddle is preferably in a path parallel to the elongation of the needles.

In a preferred embodiment of the invention, the needles are supported on a carrier, and a vibrator on the carrier is selectably operable to impart vibration to the needles in order to dislodge excess beads adhering to the exteriors of the needles. Preferably, the excess beads are dislodged just after the needles are withdrawn from the vessel so that the excess beads are returned to the vessel. However, the vibration to dislodge excess beads can take place at any time before beads in engagement with the openings of the hollow elements are deposited at the remote location.

After the beads are deposited at the remote location, the needles are positioned directly above a receptacle, and air pressure is applied to the needles to discharge liquid into a receptacle and at the same time remove any particles of broken beads or other matter that have become lodged in the internal passages of the needles.

Another aspect of the invention, is a process for arraying beads, carried out by establishing, in a vessel, a mixture comprising beads in a liquid; maintaining the beads in suspension in the liquid by reciprocation of a paddle immersed in the liquid; inserting an array of hollow elements, each having an internal passage with an opening smaller than any one of the beads, into the vessel so that all of the openings of the elements are immersed in the liquid within the vessel; drawing liquid from the vessel into each hollow element of the array through the opening thereof, until each of the openings is closed off by one of the beads; establishing a pressure differential across each opening such that the external pressure exerted on the bead closing off the opening of each hollow element is greater than the pressure within the passage of the same hollow element, thereby holding the bead in engagement with the opening; withdrawing the array of hollow elements from the vessel with beads in engagement with the openings thereof; moving the array to a remote location; and depositing the beads at the remote location.

Preferably, the reciprocation of the paddle is continued as the array of hollow elements is inserted into the vessel, and in the course of the reciprocation of the paddle, the paddle is moved to a level above a level at which the openings of the elements are located while the elements are immersed in the liquid within the vessel.

The hollow elements, which are preferably needles, are vibrated after withdrawal from the vessel, and before reaching the remote location, to dislodge excess beads adhering to the exteriors of the needles. In a preferred mode, the needles are carried to a location above a receptacle, liquid is discharged into the receptacle before the needles are returned to the bead supply vessel.

DETAILED DESCRIPTION

Figure 1:
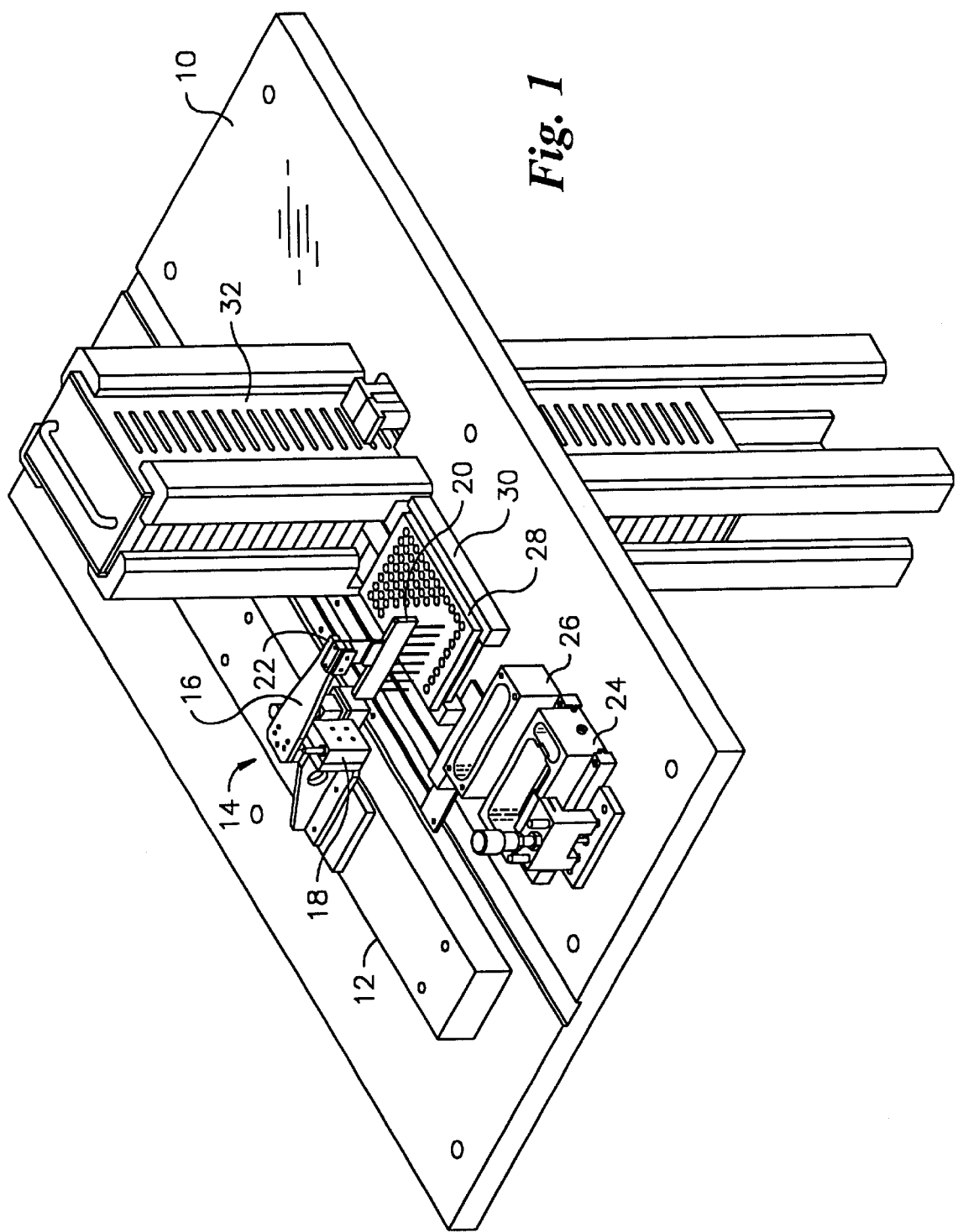
FIG. 1 is a partially schematic perspective view showing a preferred bead arraying apparatus in accordance with the invention.

As shown in FIG. 1, the apparatus comprises a bed 10 having an elongated track 12 on which a robot arm assembly 14 is slidable longitudinally. The robot arm 16 is movable vertically by an actuator 18 on the robot arm assembly. The longitudinal movement of the robot arm assembly and the vertical movement of the robot arm are under the control of a conventional robotic control (not shown), using stepping motors or other suitable positioning devices.

A needle array support 20 is rigidly suspended from an end 22 of the robot arm 16. The robot arm assembly is arranged to move the needle array in a direction parallel to track 12 from a vessel 24 to a receptacle 26, and from the receptacle 26 to a well plate 28 on a support 30. The well plate is one of a plurality of well plates moved to the well plate support one at a time from a vertically movable magazine 32, and returned to the magazine after beads are deposited in its wells.

Figure 2:
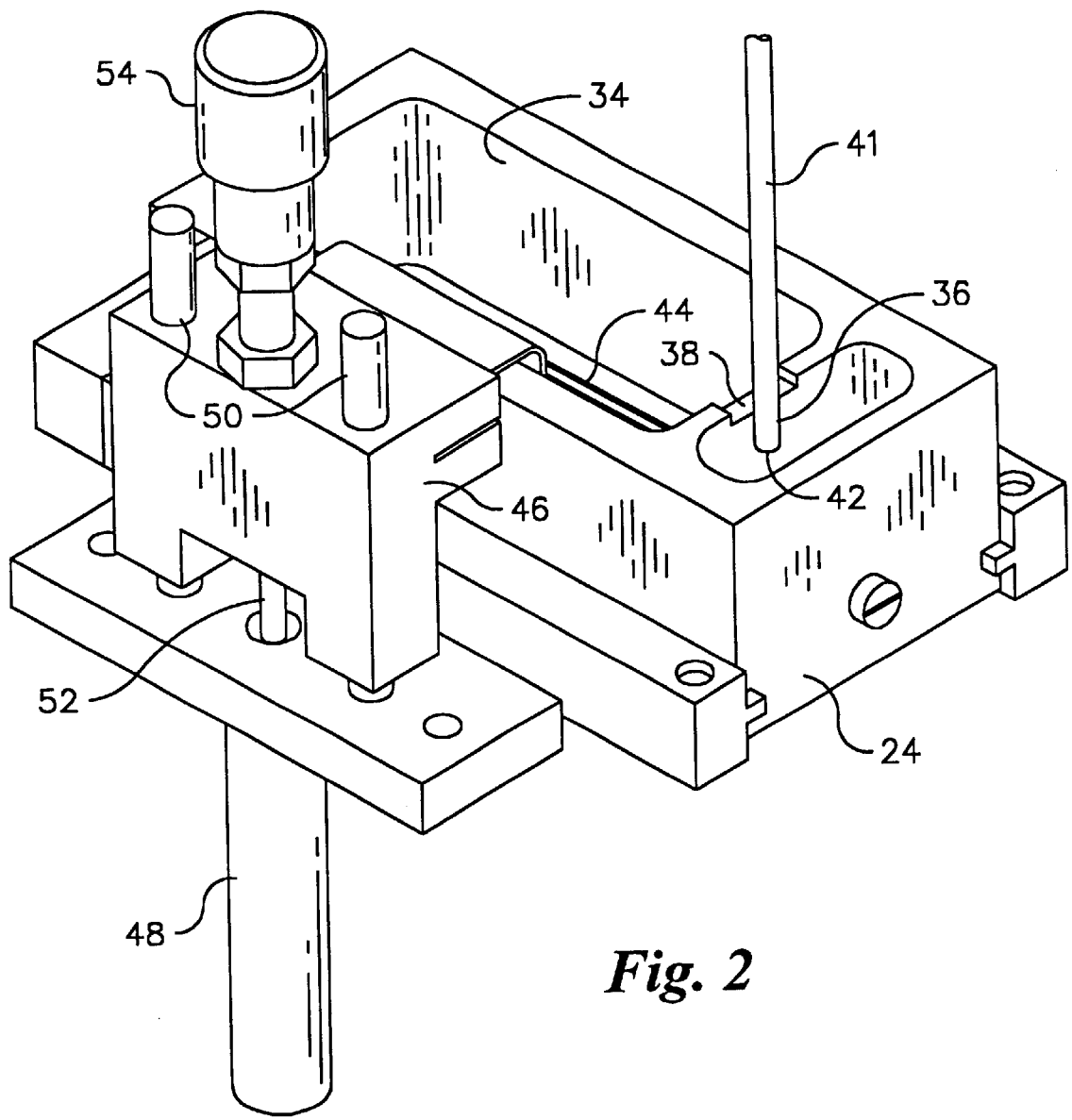
FIG. 2 is a perspective view showing the bead supply vessel, and also showing the paddle reciprocation mechanism.
Figure 3:
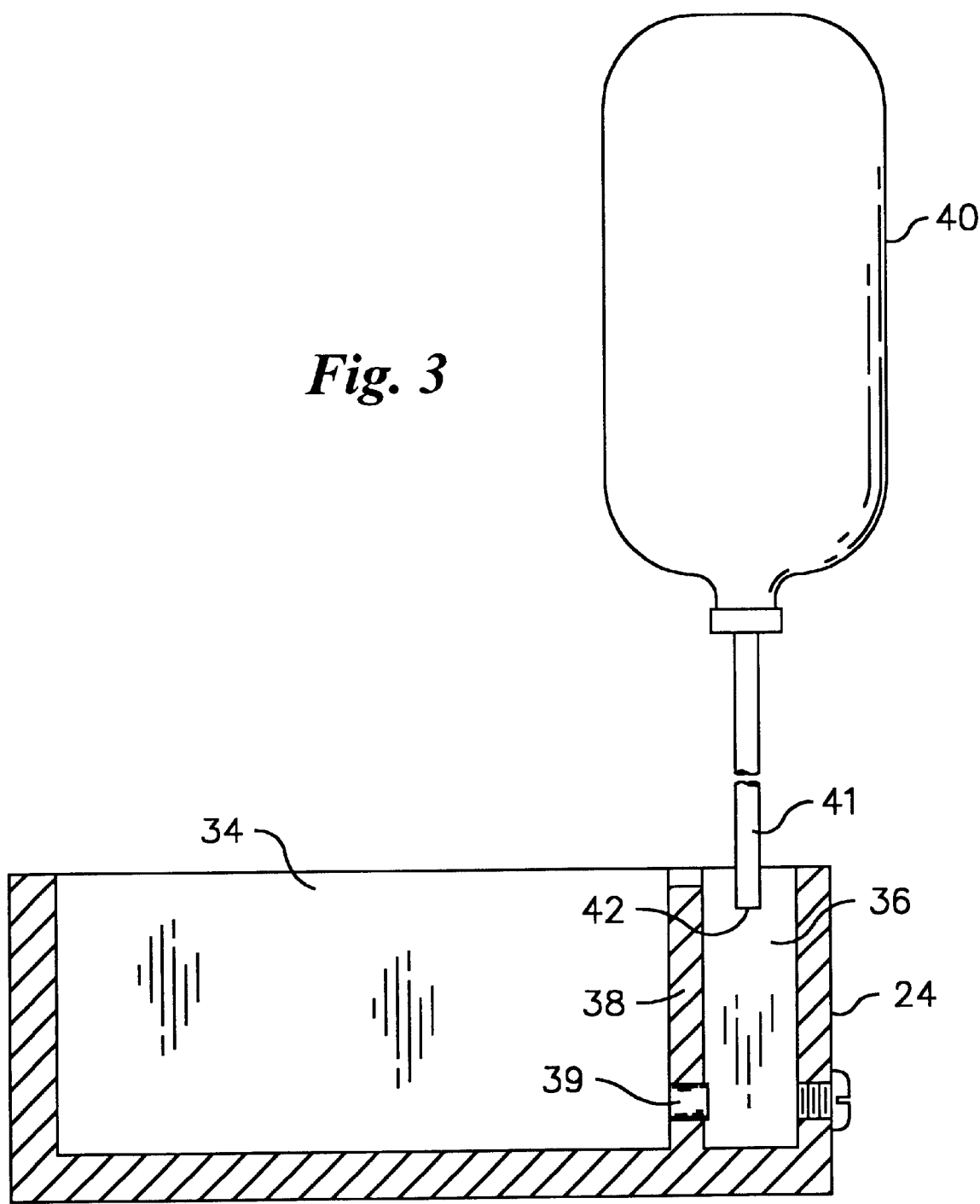
FIG. 3 is a vertical section through the bead supply vessel.

The vessel 24, shown in greater detail in FIGS. 2 and 3, is in the form of a block having a hollow space 34 for containing a liquid. The hollow space is generally rectangular in shape, and is open at the top. A smaller liquid-containing space 36 is separated from space 34 by a weir 38. The weir has a check valve 39 (FIG. 3) through which liquid can flow from space 36 to space 34, but which prevents liquid and beads from traveling in the opposite direction from space 34 to space 36. A constant liquid level is maintained in both spaces by an enclosed liquid supply container 40 (FIG. 3) connected through a tube 41 to space 36, with an opening 42 situated at the desired liquid level.

A paddle 44 within space 34 is secured to a block 46 situated alongside vessel 24. The block is reciprocable vertically by an air-operated actuator 48, and is guided by posts 50. Its height relative to the piston 52 of the actuator is adjustable by rotation of knob 54. The reciprocation of the paddle should be slow, of the order of one cycle per second, and without rapid acceleration.

Figure 4:
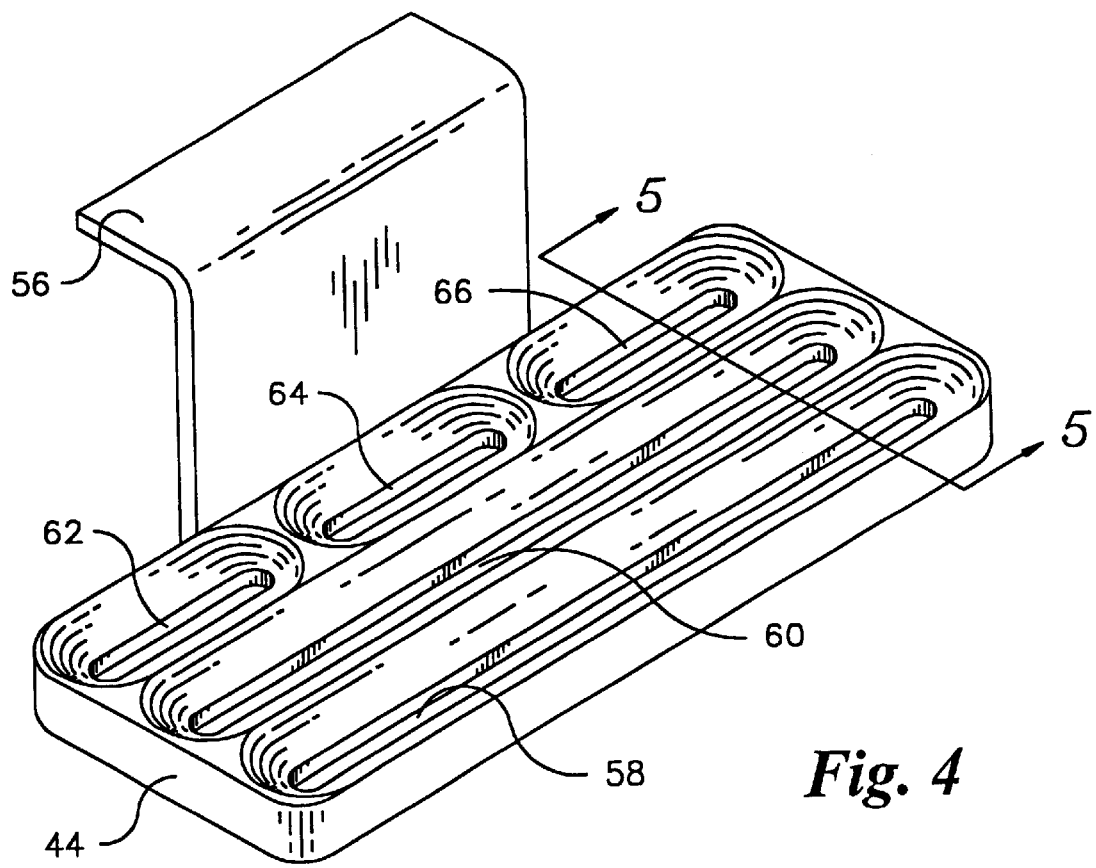
FIG. 4 is a perspective view showing the paddle.
Figure 5:
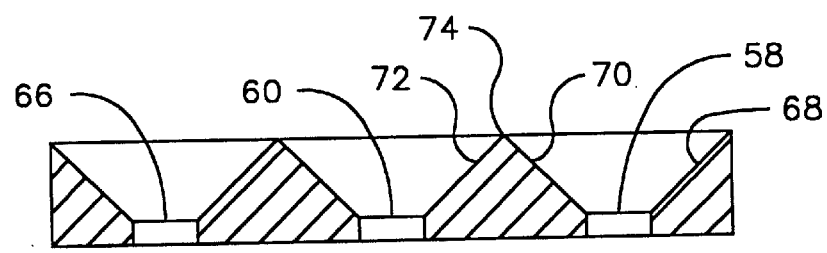
FIG. 5 is a sectional view of the paddle taken on plane 5—5 in FIG. 4.

As shown in FIGS. 4 and 5, the paddle 44 is secured to a bracket 56, and is shaped to conform to the walls of space 34 of the bead supply vessel. The paddle is generally in the form of a rectangular block with rounded corners and with a relatively small height compared to its length and width. It has two elongated slots 58 and 60, extending in spaced, parallel relation to each other, and three additional, shorter slots 62, 64 and 66, adjacent to the bracket. These shorter slots are aligned with one another and extend in parallel, spaced relation to slots 58 and 60. The interruptions between slots 62 and 64, and between slots 64 and 66, provide solid block material to accommodate fasteners (not shown) by which the paddle is secured to the bracket.

As best shown in FIG. 5, the slots have sloping walls, e.g. walls 68, 70 and 72, so that they have relatively narrow bottom openings and relatively wide upper openings. The sloping walls meet at narrow ridges, e.g. ridge 74, so that the paddle has no horizontal upper surfaces on which beads could accumulate. The paddle is reciprocated vertically within the bead supply vessel from a location in which its bottom surface is near the bottom of the vessel to a location in which its ridges are a short distance below the surface of the liquid in the vessel.

Figure 6:
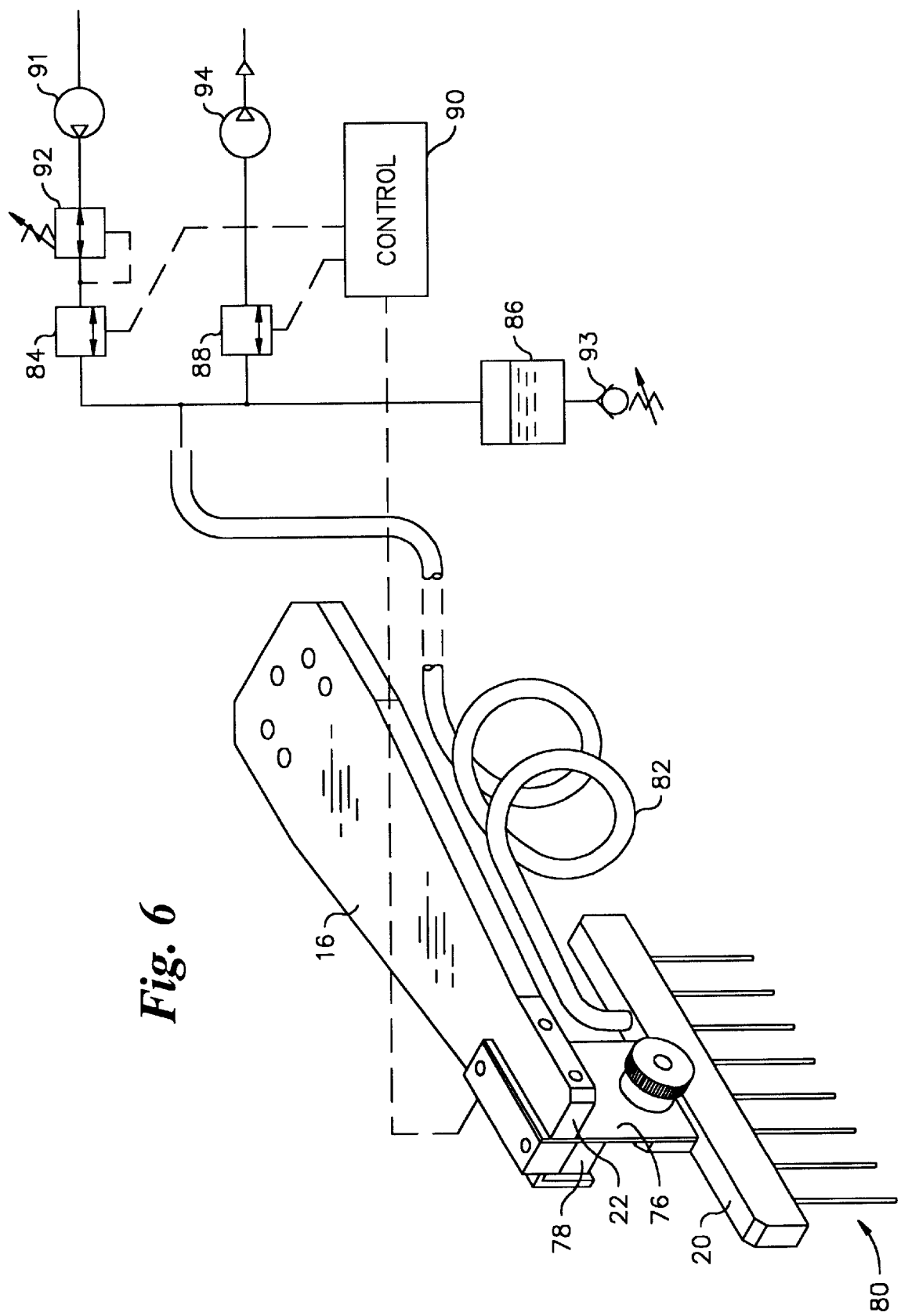
FIG. 6 is a perspective view showing the robot arm, needle array and vibrator, and also showing, schematically, the pneumatic system associated with the needles.

FIG. 6 shows the needle carrier 20 supported on arm 16 by a flexible strip 76 of spring steel. This strip is situated in close proximity to an electromagnet 78 mounted on arm 16 near end 22 of the arm. The flexible strip 76 is spaced slightly from the face of the electromagnet so that it is drawn magnetically toward the electromagnet when the electromagnet is energized.

The needle carrier has internal passages (not shown) serving as a manifold for connecting needles 80 to a flexible conduit 82. The flexible conduit is connected to two valves 84 and 88, both operated by a control 90, which can be a conventional programmable controller using a programmed logic array, a conventional software-controlled microprocessor, discrete logic circuits, relays or any of a variety of known programming schemes for operating the valves in the proper sequence to achieve the operation which will be described below. The same control can operate the arm 16, controlling its horizontal and vertical movements.

Valve 84 is connected to a compressor 91 through a pressure regulator 92. Valve 88 is connected to a vacuum pump 94. A drain reservoir 86 is connected to the common connection of valves 84 and 88 to conduit 82. The drain reservoir has a check and relief valve 93.

Control 90 is also connected to supply a rapid sequence of electrical pulses to the electromagnet in order to vibrate the needle carrier at the appropriate times.

In the operation of the apparatus just described, the paddle 44 is continuously reciprocated vertically within space 34 of the bead supply vessel 24. A liquid is maintained within the space 34 along with a supply of beads. The paddle moves from a position a short distance above the floor of space 34 to a position a short distance below the surface of the liquid. As the paddle moves downward, liquid is forced upward through the slots at a rate greater than the rate of downward movement of the paddle. Beads on the floor of the space 34 and in the liquid below the paddle are drawn upward by the upwardly moving liquid, some passing upward through the slots, and others remaining below the paddle but above the floor of the space 34. As the paddle moves upward, beads pass downward through the slots, but remain in suspension in the liquid because they do not have time to sink to the bottom before the paddle begins its downward movement.

The magazine 32 is indexed vertically to align an empty well plate with well plate support 30. The empty well plate, for example well plate 28, is pushed from the magazine to the support, and the magazine remains stationary until the well plate is returned to it after beads are deposited in its wells.

The robot arm assembly moves the needle support 20 to a position above space 34 of the bead supply vessel 24, and directly above one of the long slots in the paddle, preferably slot 60. The arm is then moved downward by actuator 18 so that the tips of the needles are immersed in the liquid.

With the tips of the needles immersed in the liquid, control 90 opens valve 88, causing pump 94 to apply a vacuum to flexible conduit 82 and, through it, to the internal passages of the needles. The tips of the needles are maintained immersed in the liquid for a time sufficient for a bead to attach to the tip of each needle. During this time, the paddle continues to reciprocate vertically, and, because the needles are directly above slot 60, the paddle can move upward past the tips of the needles.

With beads attached to the tips of the needles, the needle support is withdrawn from the liquid by actuator 18. Before the arm moves horizontally, the electromagnet 78 is activated by a short series of electrical pulses, causing carrier 20 to vibrate. Any beads or bead particles adhering to the exteriors of the needles are shaken off the needles, and drop back into the liquid in vessel 24.

After the vibration of the needles is discontinued, the arm 16 is moved horizontally, carrying the needles to a position above a row of wells in well plate 28. The actuator then lowers the carrier 20, so that the tips of the needles enter the wells. Preferably, each well has a small amount of liquid, e.g. water, in it, and the tips of the needles are immersed in the liquid. At this time, valve 88 is closed and valve 84 is opened momentarily, allowing compressor 91 to apply a short burst of pressure to the interiors of the needles to dislodge the attached beads, depositing a single bead into each well in the row.

Actuator 18 then lifts carrier 20, and the arm 16 is moved horizontally until the needles are directly above receptacle 26. At this time valve 84 is opened momentarily, allowing compressor 91 to apply a longer duration burst of pressure to the interiors of the needles to discharge liquid from the needles and any particles of broken beads or other debris lodged in the needles. The needles are then returned to vessel 24 for another bead picking cycle.

In each cycle, the needle carrier is moved to a different row of wells in the well plate until beads are deposited in all of the wells. After the deposition of beads in a given well plate is complete, the well plate is returned to magazine 32, the magazine is indexed vertically, and another well plate is moved onto support 30. The bead arraying apparatus is highly reliable, and can therefore be operated unattended as beads are deposited in all of the well plates in the magazine.

Keeping the beads in suspension by a reciprocating paddle enables the needles to pick up beads rapidly, shortening the cycle time and providing improved performance in comparison with previous bead arraying devices. The performance of the apparatus is also superior to that of alternative bead arraying devices in the reliability with which single beads are deposited in the wells. The number of empty wells and the number of wells containing multiple beads is very low. The reliability of the apparatus is enhanced by the discharge of liquid and broken beads from the needles in each cycle following deposition of beads in a row of wells.

Various modifications can be made to the apparatus described and in its operation. For example, although vertical reciprocatory movement of the paddle is preferred for simplicity, it is possible for the paddle to move in other paths, for example obliquely. In the case of oblique movement of the paddle, the needles can be disposed in line with the direction of movement of the paddle so that the paddle does not collide with the needles as it reciprocates. Alternatively, the openings in the paddle can be configured in such a way that the paddle does not collide with the needles, or range of movement of the paddle can be such that it does not interfere with the needles.

Although hollow needles are preferred for picking up beads in the apparatus of this invention, it is possible to achieve many of the objectives of the invention using alternative pick up devices such as an array of tubes or other hollow elements.

In the operation of the apparatus, the probability is high that all of the needles will pick up beads from the suspension in vessel 24 if the tips of the needles are immersed in the suspension for a sufficient time. However, it is possible to shorten the immersion time by connecting a pressure sensor to conduit 82, and to sense the presence of beads at the tips of all of the needles in the array through the sharp pressure decrease that occurs when the tips of all of the needles are closed off.

It is also possible to close off the vacuum valve 88 after the excess beads are shaken off the needles by vibration, but before the needle array is moved to the wells. The beads at the tips of the needles will remain attached because of the surface tension of the liquid inside the needles.

Still other modifications can be made to the apparatus and process described without departing from the scope of the invention as defined in the following claims.

What is claimed is:

1. An apparatus for arraying beads which comprises:
   a vessel containing a mixture comprising beads in a liquid, the vessel having an interior defined by a top opening, side walls and a bottom;
   a paddle within the vessel and immersed in the liquid therein;
   means for effecting reciprocating movement of the paddle within the liquid along a path having a vertical component;
   an array of hollow elements, each having an internal passage and an opening at an end of the internal passage, the opening being circular in shape so that it can be substantially closed off by a spherical bead, the array being insertable into the vessel so that all of the openings of the elements are immersed in the liquid within the vessel;
   means for drawing liquid from the vessel into the internal passages of the hollow elements through their openings, for establishing a pressure differential across each opening such that the external pressure exerted on a bead closing off the opening of each hollow element is greater than the pressure within the passage of the same hollow element, thereby holding the bead in engagement with the opening; and
   means for withdrawing the array of hollow elements from the vessel with beads in engagement with the openings thereof and for moving the array to a remote location for deposition of the bead;
   in which the vessel has horizontal cross-sections, and the paddle has a top and a bottom, and a horizontal projection the area of which is sufficient in comparison to the horizontal cross-sections of the vessel that movement of the paddle within the liquid along said path induces a substantial vertical movement of the liquid, whereby the beads are maintained in suspension in the liquid by the substantial vertical movement of the liquid induced by the paddle as the paddle reciprocates, and in which the paddle comprises at least two adjacent slots allowing flow of liquid through the paddle, each said slot having a relatively narrow opening at the bottom of the paddle, a relatively wide opening at the top of the paddle and sloping side walls, a side wall of one of said two adjacent slots meeting a side wall of the other of said two adjacent slots along a narrow ridge at the top of the paddle.

2. Apparatus according to claim 1, in which the hollow elements are elongated needles spaced from one another and insertable into one of said slots in the paddle, and in which the means for effecting reciprocating movement of the paddle within the liquid effects movement of the paddle through a range such that, when the needles are inserted into the vessel, the needles extend into said one of said slots in the paddle as the paddle reciprocates.

3. An apparatus for arraying beads which comprises:
   a vessel containing a mixture comprising beads in a liquid, the vessel having an interior defined by a top opening, side walls and a bottom;
   a paddle within the vessel and immersed in the liquid therein;
   means for effecting reciprocating movement of the paddle within the liquid along a path having a vertical component;
   an array of hollow elements, each having an internal passage and an opening at an end of the internal passage, the opening being circular in shape so that it can be substantially closed off by a spherical bead, the array being insertable into the vessel so that all of the openings of the elements are immersed in the liquid within the vessel;
   means for drawing liquid from the vessel into the internal passages of the hollow elements through their openings, for establishing a pressure differential across each opening such that the external pressure exerted on a bead closing off the opening of each hollow element is greater than the pressure within the passage of the same hollow element, thereby holding the bead in engagement with the opening; and
   means for withdrawing the array of hollow elements from the vessel with beads in engagement with the openings thereof and for moving the array to a remote location for deposition of the beads,
   in which the vessel has horizontal cross-sections, and the paddle has a horizontal projection the area of which is sufficient in comparison to the horizontal cross-sections of the vessel that movement of the paddle within the liquid along said path induces a substantial vertical movement of the liquid, whereby the beads are maintained in suspension in the liquid by the substantial vertical movement of the liquid induced by the paddle as it reciprocates, in which the hollow elements are elongated needles spaced from one another, in which the paddle comprises at least one opening into which the needles can extend when the needles are inserted into the vessel, and in which the means for effecting reciprocating movement of the paddle within the liquid effects movement of the paddle through a range such that, when the needles are inserted into the vessel, the needles extend into the opening of the paddle as the paddle reciprocates.

4. An apparatus according to claim 3, in which the means for effecting reciprocating movement of the paddle within the liquid, moves the paddle reciprocably in a path parallel to the elongation of the needles.

5. A process for arraying beads which comprises:
   establishing, in a vessel, a mixture comprising beads in a liquid;
   maintaining the beads in suspension in the liquid by reciprocation of a paddle immersed in the liquid;
   inserting an array of hollow elements, each having an internal passage with an opening smaller than any one of the beads, into the vessel so that all of the openings of the elements are immersed in the liquid within the vessel;

drawing liquid from the vessel into each hollow element of the array through the opening thereof, until each of the openings is closed off by one of the beads;

establishing a pressure differential across each opening such that the external pressure exerted on the bead closing off the opening of each hollow element is greater than the pressure within the passage of the same hollow element, thereby holding the bead in engagement with the opening;

withdrawing the array of hollow elements from the vessel with beads in engagement with the openings thereof;

moving the array to a remote location; and depositing the beads at the remote location;

in which the reciprocation of the paddle is continued as the array of hollow elements is inserted into the vessel, and in the course of the reciprocation of the paddle, while the hollow elements are immersed in the liquid within the vessel, the hollow elements extend into an opening extending through the paddle and the paddle is moved to a level above a level at which the openings of the elements are located.

6. A process according to claim 5 in which the reciprocation of the paddle takes place in a substantially vertical path.

7. A process according to claim 5 in which the reciprocation of the paddle within the liquid induces a substantial vertical movement of the liquid whereby the beads are maintained in suspension in the liquid by the substantial vertical movement of the liquid induced by the paddle as it reciprocates.

8. A process according to claim 5 in which the reciprocation of the paddle takes place in a substantially vertical path and induces a substantial vertical movement of the liquid whereby the beads are maintained in suspension in the liquid by the substantial vertical movement of the liquid induced by the paddle as it reciprocates.

* * * * *